US005646119A

United States Patent [19]

Oppenheim et al.

[11] Patent Number: 5,646,119
[45] Date of Patent: Jul. 8, 1997

[54] D-AMINO ACID HISTATIN-BASED PEPTIDES AS ANTI-FUNGAL AND ANTI-BACTERIAL AGENTS

[75] Inventors: Frank G. Oppenheim, Chestnut Hill; Tao Xu, Newton; Peter Spacciapoli, Newbury, all of Mass.

[73] Assignees: Periodontix, Inc., Del.; The Trustees of Boston University, Mass.

[21] Appl. No.: 485,273

[22] Filed: Jun. 7, 1995

Related U.S. Application Data

[63] Continuation-in-part of Ser. No. 287,717, Aug. 9, 1994, Pat. No. 5,486,503, which is a continuation of Ser. No. 145,030, Oct. 28, 1993, abandoned, which is a continuation of Ser. No. 786,571, Nov. 1, 1991, abandoned.

[51] Int. Cl.$^6$ .......................... A61K 38/08; A61K 38/10; C07K 7/06; C07K 7/08
[52] U.S. Cl. .................... 514/12; 514/2; 514/13; 514/14; 514/15; 530/324; 530/325; 530/326; 530/327
[58] Field of Search ................... 514/2, 12–16; 530/324–327, 328

[56] References Cited

U.S. PATENT DOCUMENTS

| | | | |
|---|---|---|---|
| 4,725,576 | 2/1988 | Pollock et al. | 514/2 |
| 5,032,574 | 7/1991 | Wilde et al. | 514/12 |
| 5,221,732 | 6/1993 | Chen et al. | 530/326 |
| 5,225,399 | 7/1993 | Zasloff et al. | 514/13 |
| 5,239,059 | 8/1993 | Zasloff et al. | 530/325 |
| 5,304,633 | 4/1994 | Tomita et al. | 530/327 |
| 5,324,716 | 6/1994 | Selsted et al. | 514/14 |
| 5,409,898 | 4/1995 | Darveau et al. | 514/13 |
| 5,424,290 | 6/1995 | Maloy et al. | 514/13 |
| 5,447,914 | 9/1995 | Travis et al. | 514/16 |
| 5,459,237 | 10/1995 | Berkowitz et al. | 530/326 |
| 5,470,950 | 11/1995 | Maloy et al. | 530/324 |
| 5,486,503 | 1/1996 | Oppenheim et al. | 514/2 |
| 5,504,190 | 4/1996 | Houghten et al. | 530/329 |
| 5,519,115 | 5/1996 | Mapelli et al. | 530/324 |
| 5,547,939 | 8/1996 | Selsted | 514/14 |
| 5,549,894 | 8/1996 | Hunt | 424/94.64 |

FOREIGN PATENT DOCUMENTS

| | | |
|---|---|---|
| 6-234653 | 8/1994 | Japan . |
| 6-287146 | 10/1994 | Japan . |

OTHER PUBLICATIONS

Murakami, Y. et. al., "Inhibitory Effects of Synthetic Histidine–Rich Peptides on Haemagglutination by Bacteroides Gingivalis 381", *Arch. Oral Biol.*, 35(9): 775–777 (1990).

Oppenheim, F.G. et. al., "Histatins, a Novel Family of Histidine–Rich Proteins in Human Paretoid Secretion", *J. Biol. Chem.*, 263 (16):7472–7477 (Jun. 1988).

Xu, T. et. al., "Anticandidal Activity of Major Human Salivary Histatins", *Infect. Immunol.*, 59 (8):2549–2554 (Aug. 1991).

Xu, T. et. al., "Anti–fungal Functional Domain of Histatin 3", *J. Dent. Res.* 70:497 (Apr. 1991).

Raj, P.A. et. al., "Salivary Histatin 5: Depnedence of Sequence, Chain Length, and Helical Confirmation for Candidacidal Activity", *J. Biol. Chem.*, 265(7):3898 (Mar. 15, 1990).

Santarpia III, R.P. et. al., "A Comparision of the Inhibition of Blastospore Viability and Germ–Tube Development in Candida Albicans by Histidine Peptides and Ketoconazole", *Arch. Oral Biol.*, 33(8):567–573 (1988).

(List continued on next page.)

*Primary Examiner*—Robert A. Wax
*Assistant Examiner*—William W. Moore
*Attorney, Agent, or Firm*—Hamilton, Brook, Smith & Reynolds, P.C.

[57] ABSTRACT

D-amino acid histatins and histatin-based peptides histatins and methods for treatment of fungal or bacterial infection are described. These D-amino acid histatins and histatin-based peptides are longer-acting anti-fungal or anti-bacterial agents than their L-enantiomeric analogues.

5 Claims, 8 Drawing Sheets

OTHER PUBLICATIONS

Santarpia III, R.P. et. al., "Preliminary Findings for In Vivo Efficacy of Salivary Histidine–Rich Polypeptides", *J. Dent. Res.*, 69:173 (Mar. 1990).

Troxler, R.F. et. al., "Structural Relationship Between Human Salivary Histatins", *J. Dent. Res.*, 69(1):2–6 (Jan. 1990).

Nishikata, M. et al., "Salivary Hisatin as an Inhibitor of a Protease Produced by the Oral Bacterium *Bacteroides gingivalis*," *Biochem. Biophys. Res. Comm.*, 174(2):625–630 (Jan. 31, 1991).

Xu, T. et al., "Structure/Function Analysis of Anti–Candida Activities of Histatin 1," *J. Dent. Res.*, 68:973 (Jun. 1989).

Xu, T. et al., "Primary Structure and Anticandidal Activity of the Major Histatin from the Parotid Secretion of the Subhuman Primate, *Macaca fascicularis*," *J. Dent. Res.*, 69(11):1717–1723 (Nov. 1990).

Zuo, Y., et al., Gene, vol. 161, "Recombinant histatins: functional domain duplication enhances candidacidal activity", pp. 87–91. 1995.

Edgerton, M., et al., Journal of Biomedical Materials Research, vol. 29, "Surface–modified poly(methyl methylacrylate) enhances adsorption and retains anticandidal activities of salivary histatin 5", pp. 1277–12895. 1995.

Histatin 1:  Asp-Pse-His-Glu-Lys-Arg-His-His-Gly-Tyr-Arg-Arg-Lys-Phe-His-Glu-Lys-His-His- Histatin 2:  Arg-Lys-Phe-His-Glu-Lys-His-His- Histatin 3:  Asp-Ser-His-Ala-Lys-Arg-His-His-Gly-Tyr-Lys-Arg-Lys-Phe-His-Glu-Lys-His-His- Histatin 4:  Arg-Lys-Phe-His-Glu-Lys-His-His- Histatin 5:  Asp-Ser-His-Ala-Lys-Arg-His-His-Gly-Tyr-Lys-Arg-Lys-Phe-His-Glu-Lys-His-His- Histatin 6:  Asp-Ser-His-Ala-Lys-Arg-His-His-Gly-Tyr-Lys-Arg-Lys-Phe-His-Glu-Lys-His-His- Histatin 7:  Arg-Lys-Phe-His-Glu-Lys-His-His- Histatin 8:  Lys-Phe-His-Glu-Lys-His-His- Histatin 9:  Arg-Lys-Phe-His-Glu-Lys-His-His- Histatin 10: Lys-Phe-His-Glu-Lys-His-His- Histatin 11: Lys-Arg-His-His-Gly-Tyr-Lys-Arg Histatin 12: Lys-Arg-His-His-Gly-Tyr-Lys Peptide 101: Lys-Arg-His-His-Gly-Tyr-Lys-Arg-Lys-Phe-His-Glu-Lys-His-His- Peptide 102: Gly-Tyr-Lys-Arg-Lys-Phe-His-Glu-Lys-His-His- Peptide 103: Lys-Arg-His-His-Gly-Tyr-Lys-Arg-Lys-Phe-His-Glu-Lys-His-His-

FIGURE 1A

```
                              10                    15
Peptide 104:                  Gly-Tyr-Lys-Arg-Lys-Phe-His-Glu-Lys-His-His-
Peptide 105:  Lys-Arg-His-His-Gly-Tyr-Lys-Arg-Lys-Phe-His-Glu-Lys-His-His
Peptide 113:  Ala-Lys-Arg-His-His-Gly-Tyr-Lys-Arg-Lys-Phe-His
Peptide 117:      Lys-Arg-His-His-Gly-Tyr-Lys-Arg-Lys-Phe-His
Peptide 118:  Ala-Lys-Arg-His-His-Gly-Tyr-Lys-Arg-Lys-Phe
Peptide 119:  Ala-Lys-Arg-His-His-Gly-Tyr-Lys-Arg-Lys
Peptide 120:  Ala-Lys-Arg-His-His-Gly-Tyr-Lys-Arg
Peptide 129:      Lys-Arg-His-His-Gly-Tyr-Lys-Arg-Lys-Phe 20                      25                    30                    35
Histatin 1:   Ser-His-Arg-Glu-Phe-Pro-Phe-Tyr-Gly-Asp-Tyr-Gly-Ser-Asn-Tyr-Leu-Tyr-Asp-Asn
Histatin 2:   Ser-His-Arg-Glu-Phe-Pro-Phe-Tyr-Gly-Asp-Tyr-Gly-Ser-Asn-Tyr-Leu-Tyr-Asp-Asn
Histatin 3:   Ser-His-Arg-Gly-Tyr-Arg-Ser-Asn-Tyr-Leu-Tyr-Asp-Asn
Histatin 4:   Ser-His-Arg-Gly-Tyr-Arg-Ser-Asn-Tyr-Leu-Tyr-Asp-Asn
Histatin 5:   Ser-His-Arg-Gly-Tyr
Histatin 6:   Ser-His-Arg-Gly-Tyr-Arg
Histatin 7:   Ser-His-Arg-Gly-Tyr
```

FIGURE 1B

```
                20                      25
Histatin 8:     Ser-His-Arg-Gly-Tyr
Histatin 9:     Ser-His-Arg-Gly-Tyr-Arg
Histatin 10:    Ser-His-Arg-Gly-Tyr-Arg
Peptide 101:    Ser-His-Arg-Gly-Tyr-Arg
Peptide 102:    Ser-His-Arg-Gly-Tyr-Arg
Peptide 103:    Ser-His-Arg
Peptide 104:    Ser-His-Arg
```

FIGURE 1C

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /product="PSE"

( i x ) FEATURE:
        ( A ) NAME/KEY: Region
        ( B ) LOCATION: 1..38
        ( D ) OTHER INFORMATION: /note="At least one amino acid must have a D configuration."

( x i ) SEQUENCE DESCRIPTION: SEQ ID NO:1:

```
Asp Xaa His Glu Lys Arg His His Gly Tyr Arg Arg Lys Phe His Glu
 1               5                  10                      15

Lys His His Ser His Arg Glu Phe Pro Phe Tyr Gly Asp Tyr Gly Ser
                20                  25                  30

Asn Tyr Leu Tyr Asp Asn
                35
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..27
        ( D ) OTHER INFORMATION: /note="At least one amino acid must have a D configuration"

( x i ) SEQUENCE DESCRIPTION: SEQ ID NO:2:

```
Arg Lys Phe His Glu Lys His His Ser His Arg Glu Phe Pro Phe Tyr
 1               5                  10                      15

Gly Asp Tyr Gly Ser Asn Tyr Leu Tyr Asp Asn
                20                  25
```

( 2 ) INFORMATION FOR SEQ ID NO:3:

( i ) SEQUENCE CHARACTERISTICS:
    ( A ) LENGTH: 32 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Region
    ( B ) LOCATION: 1..32
    ( D ) OTHER INFORMATION: /note="At least one amino acid
        must have a D configuration."

( x i ) SEQUENCE DESCRIPTION: SEQ ID NO:3:

```
Asp  Ser  His  Ala  Lys  Arg  His  His  Gly  Tyr  Lys  Arg  Lys  Phe  His  Glu
 1              5                        10                       15
Lys  His  His  Ser  His  Arg  Gly  Tyr  Arg  Ser  Asn  Tyr  Leu  Tyr  Asp  Asn
               20                       25                       30
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..21
        ( D ) OTHER INFORMATION: /note="At least one amino acid
            must have a D configuration."

( x i ) SEQUENCE DESCRIPTION: SEQ ID NO:4:

```
Arg  Lys  Phe  His  Glu  Lys  His  His  Ser  His  Arg  Gly  Tyr  Arg  Ser  Asn
 1              5                        10                       15
Tyr  Leu  Tyr  Asp  Asn
               20
```

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..24
        ( D ) OTHER INFORMATION: /note="At least one amino acid
            must have a D configuration."

( x i ) SEQUENCE DESCRIPTION: SEQ ID NO:5:

```
Asp  Ser  His  Ala  Lys  Arg  His  His  Gly  Tyr  Lys  Arg  Lys  Phe  His  Glu
 1              5                        10                       15
Lys  His  His  Ser  His  Arg  Gly  Tyr
               20
```

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( C ) STRANDEDNESS:

(D) TOPOLOGY: linear (ii) MOLECULE TYPE: peptide (ix) FEATURE:
 (A) NAME/KEY: Region
 (B) LOCATION: 1..25
 (D) OTHER INFORMATION: /note="At least one amino acid
  must have a D configuration."

(xi) SEQUENCE DESCRIPTION: SEQ ID NO:6:

```
Asp Ser His Ala Lys Arg His His Gly Tyr Lys Arg Lys Phe His Glu
 1               5                  10                      15

Lys His His Ser His Arg Gly Tyr Arg
             20                  25
```

(2) INFORMATION FOR SEQ ID NO:7:

(i) SEQUENCE CHARACTERISTICS:
  (A) LENGTH: 13 amino acids
  (B) TYPE: amino acid
  (C) STRANDEDNESS:
  (D) TOPOLOGY: linear (ii) MOLECULE TYPE: peptide (ix) FEATURE:
  (A) NAME/KEY: Region
  (B) LOCATION: 1..13
  (D) OTHER INFORMATION: /note="At least one amino acid
   must have a D configuration."

(xi) SEQUENCE DESCRIPTION: SEQ ID NO:7:

```
Arg Lys Phe His Glu Lys His His Ser His Arg Gly Tyr
 1               5                  10
```

(2) INFORMATION FOR SEQ ID NO:8:

(i) SEQUENCE CHARACTERISTICS:
  (A) LENGTH: 12 amino acids
  (B) TYPE: amino acid
  (C) STRANDEDNESS:
  (D) TOPOLOGY: linear (ii) MOLECULE TYPE: peptide (ix) FEATURE:
  (A) NAME/KEY: Region
  (B) LOCATION: 1..12
  (D) OTHER INFORMATION: /note="At least one amino acid
   must have a D configuration."

(xi) SEQUENCE DESCRIPTION: SEQ ID NO:8:

```
Lys Phe His Glu Lys His His Ser His Arg Gly Tyr
 1               5                  10
```

(2) INFORMATION FOR SEQ ID NO:9:

(i) SEQUENCE CHARACTERISTICS:
  (A) LENGTH: 14 amino acids
  (B) TYPE: amino acid
  (C) STRANDEDNESS:
  (D) TOPOLOGY: linear (ii) MOLECULE TYPE: peptide (ix) FEATURE:
  (A) NAME/KEY: Region
  (B) LOCATION: 1..14
  (D) OTHER INFORMATION: /note="At least one amino acid
   must have a D configuration."

(xi) SEQUENCE DESCRIPTION: SEQ ID NO:9:

```
Arg  Lys  Phe  His  Glu  Lys  His  His  Ser  His  Arg  Gly  Tyr  Arg
1              5                        10
```

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i x ) FEATURE:
        ( A ) NAME/KEY: Region
        ( B ) LOCATION: 1..13
        ( D ) OTHER INFORMATION: /note="At least one amino acid
            must have a D configuration."

( x i ) SEQUENCE DESCRIPTION: SEQ ID NO:10:

```
Lys  Phe  His  Glu  Lys  His  His  Ser  His  Arg  Gly  Tyr  Arg
1              5                        10
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..8
        ( D ) OTHER INFORMATION: /note="At least one amino acid
            must have a D configuration."

( x i ) SEQUENCE DESCRIPTION: SEQ ID NO:11:

```
Lys  Arg  His  His  Gly  Tyr  Lys  Arg
1              5
```

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: 1..7
        ( D ) OTHER INFORMATION: /note="At least one amino acid
            must have a D configuration."

( x i ) SEQUENCE DESCRIPTION: SEQ ID NO:12:

```
Lys  Arg  His  His  Gly  Tyr  Lys
1              5
```

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:

(A) NAME/KEY: Region
(B) LOCATION: 1..21
(D) OTHER INFORMATION: /note="At least one amino must
have a D configuration."

( x i ) SEQUENCE DESCRIPTION: SEQ ID NO:13:

```
Lys  Arg  His  His  Gly  Tyr  Lys  Arg  Lys  Phe  His  Glu  Lys  His  His  Ser
1                   5                        10                        15

His  Arg  Gly  Tyr  Arg
               20
```

( 2 ) INFORMATION FOR SEQ ID NO:14:

( i ) SEQUENCE CHARACTERISTICS:
(A) LENGTH: 17 amino acids
(B) TYPE: amino acid
(C) STRANDEDNESS:
(D) TOPOLOGY: linear ( i i ) MOLECULE TYPE: peptide ( i x ) FEATURE:
(A) NAME/KEY: Region
(B) LOCATION: 1..17
(D) OTHER INFORMATION: /note="At least one amino acid
must have a D configuration."

( x i ) SEQUENCE DESCRIPTION: SEQ ID NO:14:

```
Gly  Tyr  Lys  Arg  Lys  Phe  His  Glu  Lys  His  His  Ser  His  Arg  Gly  Tyr
1                   5                        10                        15

Arg
```

( 2 ) INFORMATION FOR SEQ ID NO:15:

( i ) SEQUENCE CHARACTERISTICS:
(A) LENGTH: 18 amino acids
(B) TYPE: amino acid
(C) STRANDEDNESS:
(D) TOPOLOGY: linear ( i i ) MOLECULE TYPE: peptide ( i x ) FEATURE:
(A) NAME/KEY: Region
(B) LOCATION: 1..18
(D) OTHER INFORMATION: /note="At least one amino acid
must have a D configuration."

( x i ) SEQUENCE DESCRIPTION: SEQ ID NO:15:

```
Lys  Arg  His  His  Gly  Tyr  Lys  Arg  Lys  Phe  His  Glu  Lys  His  His  Ser
1                   5                        10                        15

His  Arg
```

( 2 ) INFORMATION FOR SEQ ID NO:16:

( i ) SEQUENCE CHARACTERISTICS:
(A) LENGTH: 14 amino acids
(B) TYPE: amino acid
(C) STRANDEDNESS:
(D) TOPOLOGY: linear ( i i ) MOLECULE TYPE: peptide ( i x ) FEATURE:
(A) NAME/KEY: Region
(B) LOCATION: 1..14
(D) OTHER INFORMATION: /note="At least one amino acid
must have a D configuration."

( x i ) SEQUENCE DESCRIPTION: SEQ ID NO:16:

```
Gly Tyr Lys Arg Lys Phe His Glu Lys His His Ser His Arg
1               5                   10
```

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Region
        (B) LOCATION: 1..15
        (D) OTHER INFORMATION: /note="At least one amino acid
        must have a D configuration."

(xi) SEQUENCE DESCRIPTION: SEQ ID NO:17:

```
Lys Arg His His Gly Tyr Lys Arg Lys Phe His Glu Lys His His
1               5                   10                  15
```

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Region
        (B) LOCATION: 1..12
        (D) OTHER INFORMATION: /note="At least one amino acid
        must have a D configuration."

(xi) SEQUENCE DESCRIPTION: SEQ ID NO:18:

```
Ala Lys Arg His His Gly Tyr Lys Arg Lys Phe His
1               5                   10
```

(2) INFORMATION FOR SEQ ID NO:19:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Region
        (B) LOCATION: 1..11
        (D) OTHER INFORMATION: /note="At least one amino acid
        must have a D configuration."

(xi) SEQUENCE DESCRIPTION: SEQ ID NO:19:

```
Lys Arg His His Gly Tyr Lys Arg Lys Phe His
1               5                   10
```

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide

```
        ( i x ) FEATURE:
                ( A ) NAME/KEY: Region
                ( B ) LOCATION: 1..11
                ( D ) OTHER INFORMATION: /note="At least one amino acid
                        must have a D configuration."

( x i ) SEQUENCE DESCRIPTION: SEQ ID NO:20:

Ala  Lys  Arg  His  His  Gly  Tyr  Lys  Arg  Lys  Phe
    1                   5                        10

( 2 ) INFORMATION FOR SEQ ID NO:21:

( i ) SEQUENCE CHARACTERISTICS:
                ( A ) LENGTH: 10 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: Region
                ( B ) LOCATION: 1..10
                ( D ) OTHER INFORMATION: /note="At least one amino acid
                        must have a D configuration."

( x i ) SEQUENCE DESCRIPTION: SEQ ID NO:21:

Ala  Lys  Arg  His  His  Gly  Tyr  Lys  Arg  Lys
    1                   5                        10

( 2 ) INFORMATION FOR SEQ ID NO:22:

( i ) SEQUENCE CHARACTERISTICS:
                ( A ) LENGTH: 9 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: Region
                ( B ) LOCATION: 1..9
                ( D ) OTHER INFORMATION: /note="At least one amino acid
                        must have a D configuration."

( x i ) SEQUENCE DESCRIPTION: SEQ ID NO:22:

Ala  Lys  Arg  His  His  Gly  Tyr  Lys  Arg
    1                   5

( 2 ) INFORMATION FOR SEQ ID NO:23:

( i ) SEQUENCE CHARACTERISTICS:
                ( A ) LENGTH: 10 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: Region
                ( B ) LOCATION: 1..10
                ( D ) OTHER INFORMATION: /note="At least one amino acid
                        must have a D configuration."

( x i ) SEQUENCE DESCRIPTION: SEQ ID NO:23:

Lys  Arg  His  His  Gly  Tyr  Lys  Arg  Lys  Phe
    1                   5                        10
```

D-AMINO ACID HISTATIN-BASED PEPTIDES AS ANTI-FUNGAL AND ANTI-BACTERIAL AGENTS

RELATED APPLICATIONS

This is a Continuation-in-Part of U.S. Ser. No. 08/287,717, filed Aug. 9, 1994, and issued as U.S. Pat. No. 5,486,503, which is a File Wrapper Continuation of U.S. Ser. No. 08/145,030, filed Oct. 28, 1993 (now abandoned), which is a File Wrapper Continuation of U.S. Ser. No. 07/786,571, filed Nov. 1, 1991 (now abandoned), the contents of which are incorporated herein by reference in their entirety.

GOVERNMENT SUPPORT

The invention described herein was supported in whole or in part by Grant No. DE07652 from the National Institutes of Health, which have certain rights in the invention.

BACKGROUND OF THE INVENTION

The family of naturally occurring human histatins is a group of twelve low molecular weight, abundant in histidine, peptides found in human submandibular and parotid salivary secretions (Oppenheim et al. (1986), *J. Biol. Chem.* 261: 1177–1182; Oppenheim et al. (1988), *J. Biol. Chem.* 263: 7472–7477; Troxler et al. (1990), *J. Dent. Res.* 69: 2–6). The primary structure of the major family members (histatins 1, 3, and 5; 70–80% of the whole family) has shown that these proteins consist of 38, 32 and 24 amino acid residues, respectively. There is a high degree of homology among these three major histatins. Histatin 5 results from post-translational cleavage of histatin 3. Many of the smaller members of the histatin family may also, in fact, originate by post-translational proteolysis of histatins 1, 3 and 5 (Oppenheim et al. (1989), *Human Saliva: Clinical Chemistry and Microbiology Vol.* 1 CRC Press, Boca Raton, Fla., ed. Tenovuo, J. O.; Lal et al. (1992), *Arch. Oral Biol.* 37: 7–13). The genes that encode histatins 1 and 3 have been localized chromosomally (vanderSpek et al., (1989), *Am. J. Hum. Genet.* 45: 381–387) and sequenced (Sabatini, L. M. et al. (1989), *Biochem. Biophys. Res. Comm.* 160:495–502). Histatins 1 and 3 appear to be derived from separate genes.

The three major human histatins exhibit specific antimicrobial activities towards diverse oral microbiota. These histatins, at physiological concentrations, are capable of killing *Candida albicans* in both blastopore and mycelial forms (Pollock, J. J. et al. (1984), *Infect. Immun.* 44:702–707; Xu, T. et al. (1991), *Infect. Immun.* 59 (8): 2549–2554). Histatins are also capable of killing oral bacteria, including *Streptococcus mutans* (MacKay, B. J. et al. (1984), *Infect. Immun.* 44:695–701; Xu, T. et al. (1990), *J. Dent. Res.* 69: 239), *Porphyromonas gingivalis* (Colon et al. (1993), *J. Dent. Res.* 72: 322) and *Actinomyces viscosus* (Kalpidis et al. (1992) *J. Dent. Res.* 72: 305).

Infection with the yeast *Candida albicans* is a prevalent and, in some cases, life-threatening condition affecting otherwise healthy and immuno-compromised patients. Candidal vaginitis is estimated to affect 15 to 55% of healthy young women. Candidal infections often occur in diabetics, during pregnancy, and following medication with antibiotics, steroid hormones, or oral contraceptives. (Tapper-Jones, L. M. et al. (1981) *J. Clin. Pathol.* 34:706–11; Sobel, J. D. et al. (1984) *Infect. Immun.* 44:576–580). Oral candidiasis is an early opportunistic infection of Acquired Immune Deficiency Syndrome (AIDS) in individuals infected with human immunodeficiency virus type 1, as well as a complication of radiation and chemotherapy in cancer patients. (Yeh, C.-K. et al. (1988) *J. of Acquired Immune Deficiency Syndromes* 1:361–366). In addition, candidal infection of denture wearers plays a primary role in dental stomatitis, a prevalent oral problem among the elderly. (Pollock, J. J. et al. (1990) *NYS Dental J.* 56:36–38). Candidal infections of skin and urethra are widespread problems. In patients in intensive care and immuno-compromised patients, systemic fungal infection often leads to death, since there are few safe and effective anti-fungal pharmaceuticals for intravenous use. (Burnie, J. P. et al. (1985) *British Medical Journal* 290:746–748). Similarly, infections with various bacterial species can cause severe disease states and even death.

Although several anti-fungal agents (e.g., clotrimazole, miconazole, ketoconazole, and nystatin) and anti-bacterial agents (penicillin, streptomycin, tetracycline and chlorhexidine) are currently available, these agents are not completely effective, can lead to drug resistant organisms and can produce adverse side effects. Many are not appropriate for oral or systemic administration. Thus, a potent, naturally occurring anti-fungal or anti-bacterial substance would provide a significant improvement in the treatment of microbial infection.

SUMMARY OF THE INVENTION

This invention is based on substantially pure peptides which have anti-candidal or anti-bacterial activity equal to or greater than that of naturally occurring histatins but are smaller in size. These peptides have one or more D-amino acids in their amino acid sequences. These peptides represent defined portions of the amino acid sequences of naturally occurring human histidine-rich salivary proteins called histatins, and will be referred to herein as D-amino acid histatin-based peptides. As demonstrated herein, these D-amino acid histatin-based peptides have been shown to be superior in anti-candidal or anti-bacterial activity over the naturally occurring histatins. Thus, this invention provides compositions for treatment of fungal or bacterial infection comprising histatin-based peptides with defined amino acid sequences containing one or more D-amino acids. The D-amino acid peptides with significant anti-fungal or anti-bacterial activities have sequence portions of at least 8 amino acids and have the amino acid sequences of naturally occurring human histatins or histatin-based peptides derived from these histatins.

BRIEF DESCRIPTION OF FIGURES

FIG. 1A–1C shows the amino acid sequences of human histatins and peptides 101, 102, 103, 104, 105, 113, 117, 118, 119, 120 and 129.

DETAILED DESCRIPTION OF THE INVENTION

Figure 2:
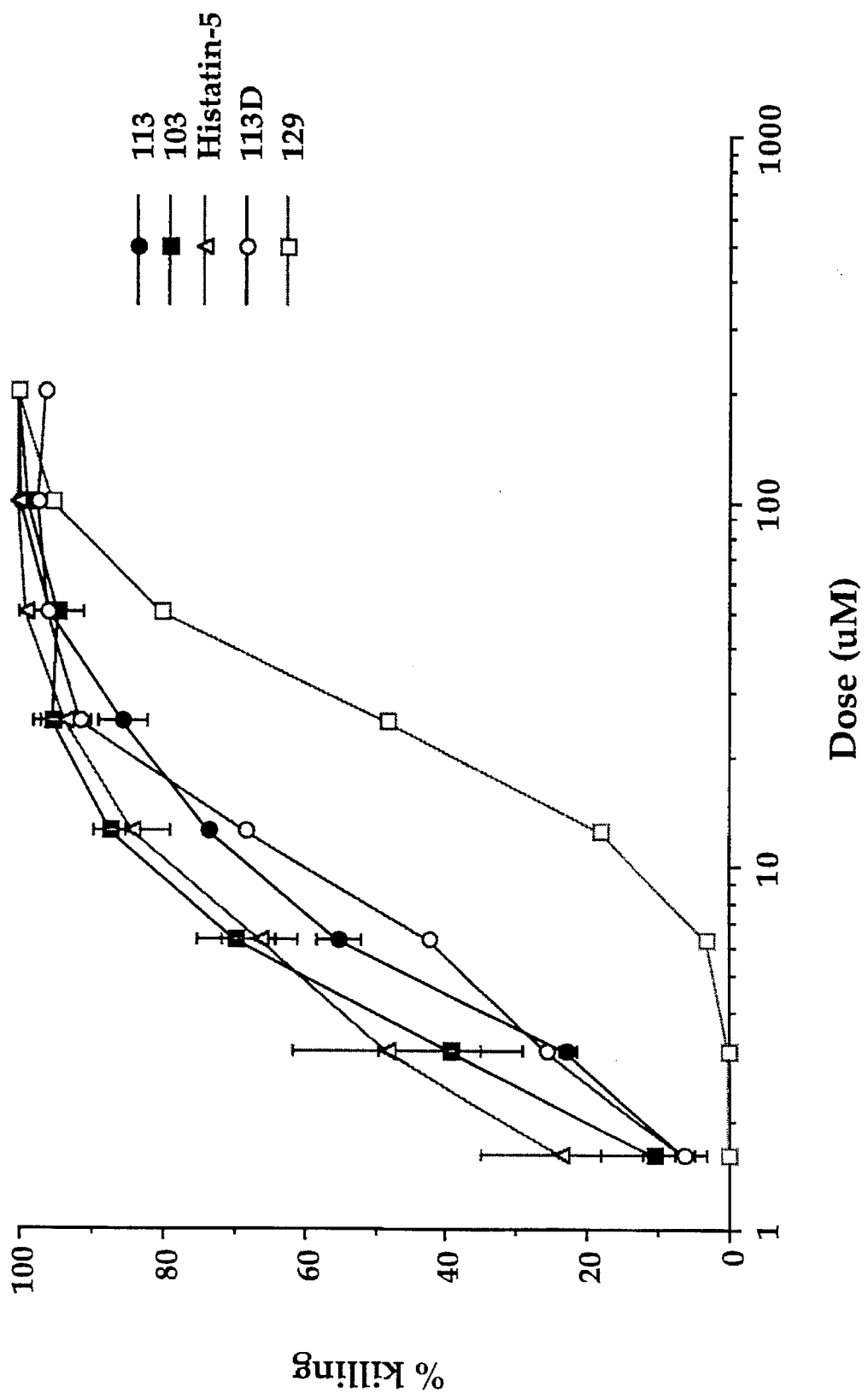
FIG. 2 is a graph that shows the % killing of *C. albicans* blastoconidia as a function of the concentration of histatin-5, peptide 103, peptide 113, peptide 113D and peptide 129.
Figure 3:
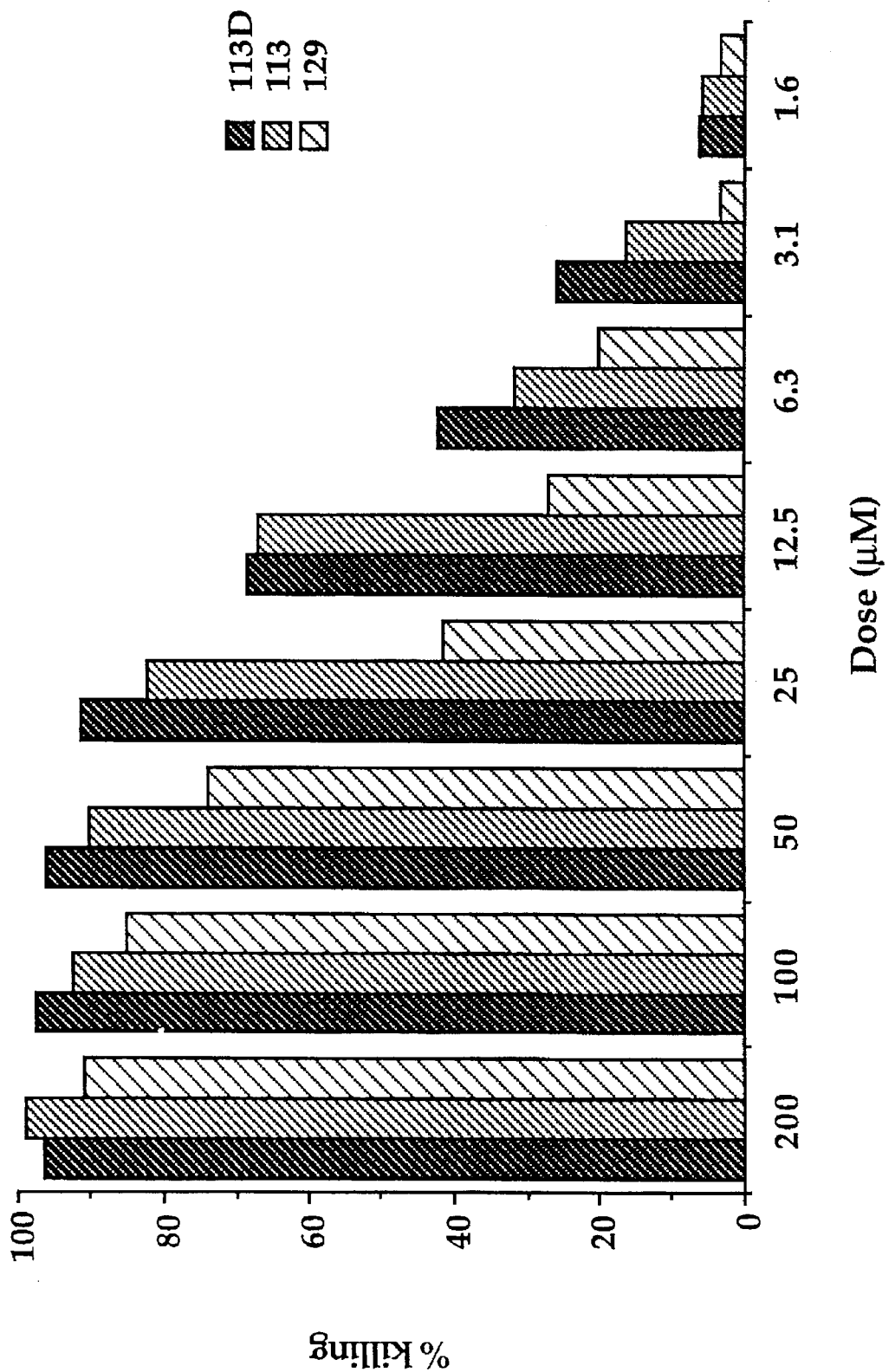
FIG. 3 is a bar graph that shows the % killing of *C. albicans* blastoconidia for different concentrations of peptide 113, peptide 113D and peptide 129.

This invention relates to peptides which have anti-fungal or anti-bacterial activity, in which the amino acid sequences represent defined portions of the amino acid sequences of naturally occurring human histidine-rich salivary proteins called histatins and where one or more of the amino acids of the amino acid sequences is of the D form. (Histatins are also referred to in the literature as histidine-rich proteins or HRPs.) Histatins are major salivary proteins which are synthesized in the parotid and submandibular-sublingual secretory glands of humans and 01d World monkeys. (Azen, E. A. (1978) *Biochem. Genet.* 16:79–99). Histatins are believed to be part of an extraimmunologic defense system of the oral cavity. The anti-fungal activity of histatins, as well as their inhibitory effect on several oral bacteria (such as the cariogenic *Streptococcus mutans* and the periodontal pathogen *Porphyromonas gingivalis*), have been demonstrated in vitro. In addition, the observation that polyhistidine peptides inactivate herpes simplex virus in vitro and that whole saliva contains inhibitors of human immunodeficiency virus suggests the possibility that histatins may have anti-viral activity. These in vitro studies support potential clinical use of compositions containing histatins or histatin-based peptides that contain one or more D-amino acids for the treatment of local and systemic candidal infection, oral bacterial diseases, such as caries and periodontitis, systemic bacterial infection and viral infection. Vaginal, urethral, skin, oral or ophthalmic fungal or bacterial infections are particularly susceptible to D-amino acid histatin-based peptide therapy. Microbes which are specifically amenable to D-amino histatin-based peptide therapy are:

a) *Candida albicans;*
b) *Actinomyces actinomycetemcomitans;*
c) *Actinomyces viscosus;*
d) *Bacteroides forsythus;*
e) *Bacteriodes fragilis;*
f) *Bacteriodes gracilis;*
g) *Bacteriodes ureolyticus;*
h) *Campylobacter concisus;*
i) *Campylobacter rectus;*
j) *Campylobacter showae;*
k) *Campylobacter sputorum;*
l) *Capnocytophaga gingivalis;*
m) *Capnocytophaga ochracea;*
n) *Capnocytophaga sputigena;*
o) *Clostridium histolyticum;*
p) *Eikenella corrodens;*
q) *Eubacterium nodatum;*
r) *Fusobacterium nucleatum;*
s) *Fusobacterium periodonticum;*
t) *Peptostreptococcus micros;*
u) *Porphyromonas endodontalis;*
v) *Porphyromonas gingivalis;*
w) *Prevotella intermedia;*
x) *Prevotella nigrescens;*
y) *Propionibacterium acnes;*
z) *Pseudomonas aeruginosa;*
aa) *Selenomonas noxia;*
bb) *Staphylococcus aureus;*
cc) *Streptococcus constellatus;*
dd) *Streptococcus gordonii;*
ee) *Streptococcus intermedius;*
ff) *Streptococcus mutans;*
gg) *Streptococcus oralis;*
hh) *Streptococcus pneumonia;*
ii) *Streptococcus sanguis;*
kk) *Treponema denticola;*
ll) *Treponema pectinovorum;*
mm) *Treponema socranskii;*
nn) *Veillonella parvula;* and
oo) *Wolinella succinogenes.*

The human histatin proteins have been isolated and sequenced. They have been shown to be a family of twelve related low molecular weight proteins. Comparison of the amino acid sequences of the histatins suggests that histatin 2 and histatins 4–12 may have originated from specific proteolytic cleavage of histatin 1 and histatin 3, respectively. (Oppenheim, F. G. et al. (1988), *J. Biol. Chem.* 263:7472–77; Troxler, R. F. et al. (1990), *J. Dent. Res.* 69(1):2–6). Cloning and sequence analysis of histatin cDNAs further suggest that the histatins are encoded by two homologous genetic loci, whose primary products are histatins 1 and 3. (Sabatini, L. M. et al. (1989), *Biochem. Biophys. Res. Comm.* 160:495–502; Vanderspek, J. C. et al. (1990), *Arch. Oral Biol.* 35(2):137–43).

The amino acid sequences of the anti-fungal and anti-bacterial peptides of this invention represent all or defined portions of the amino acid sequence of peptide 113 (SEQ ID NO: 18). Specific preferred embodiments of this invention are histatin 1 (SEQ ID NO: 1), histatin 3 (SEQ ID NO: 3), histatin 5 (SEQ ID NO: 5), histatin 9 (SEQ ID NO: 9), peptide 101 (SEQ ID NO: 13), peptide 102 (SEQ ID NO: 14), peptide 103 (SEQ ID NO: 15), peptide 104 (SEQ ID NO: 16), peptide 105 (SEQ ID NO: 17), peptide 113 (SEQ ID NO: 18), histatin 11 (SEQ ID NO: 11), peptide 129 (SEQ ID NO: 23), peptide 117 (SEQ ID NO: 19), peptide 118 (SEQ ID NO: 20), peptide 119 (SEQ ID NO: 21), and peptide 120 (SEQ ID NO: 22). The amino acid sequences of these preferred peptides are shown in FIG. 1A–1C. Combinations of two or more of these D-amino acid peptides are also effective as anti-fungal or anti-bacterial compositions and are included as compositions of the invention. The D-amino acid peptides can be chemically synthesized. These D-amino acid peptides can be altered by minor chemical modifications, such as by adding small substituents or by modifying one or more of the covalent bonds within or between the amino acid residues, without significantly diminishing the anti-fungal or anti-bacterial activities of the peptides. Particularly useful modifications are acetylation of the amino terminus of the peptide or amidation of the carboxyl terminus of the peptide. A combination of both modifications is especially useful. Such modifications appear to further increase the biological half-life of the peptides, beyond that afforded by incorporating D-amino acids in the sequence structure, before degradation, encapsulation, internalization or excretion occurs.

Figure 4:
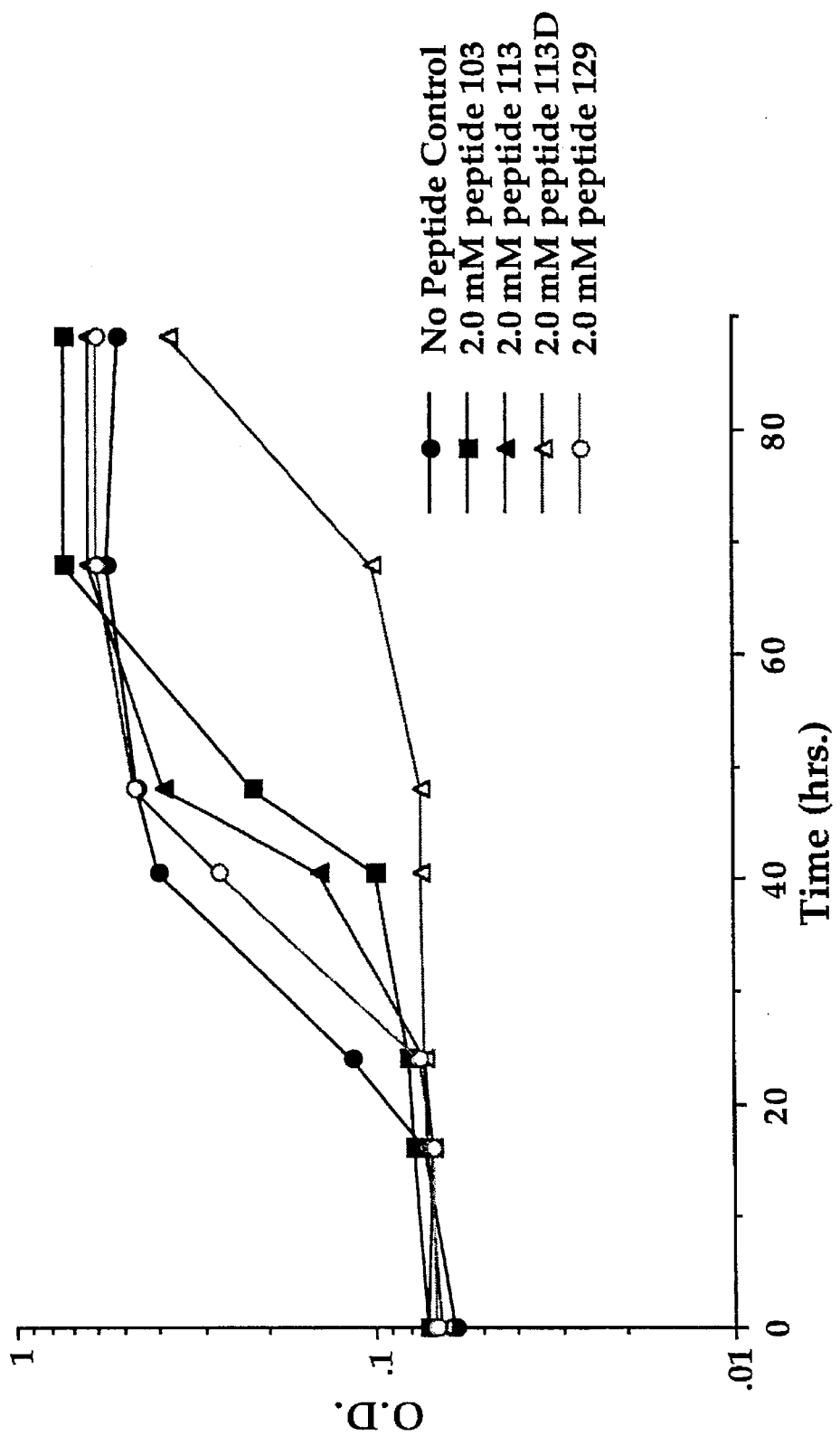
FIG. 4 is a graph that shows the amount of growth inhibition of *P. gingivalis* as a function of time for 2 mM concentrations of peptide 103, peptide 113, peptide 113D, and peptide 129, as well as when no histatin-based peptide is present.
Figure 5:
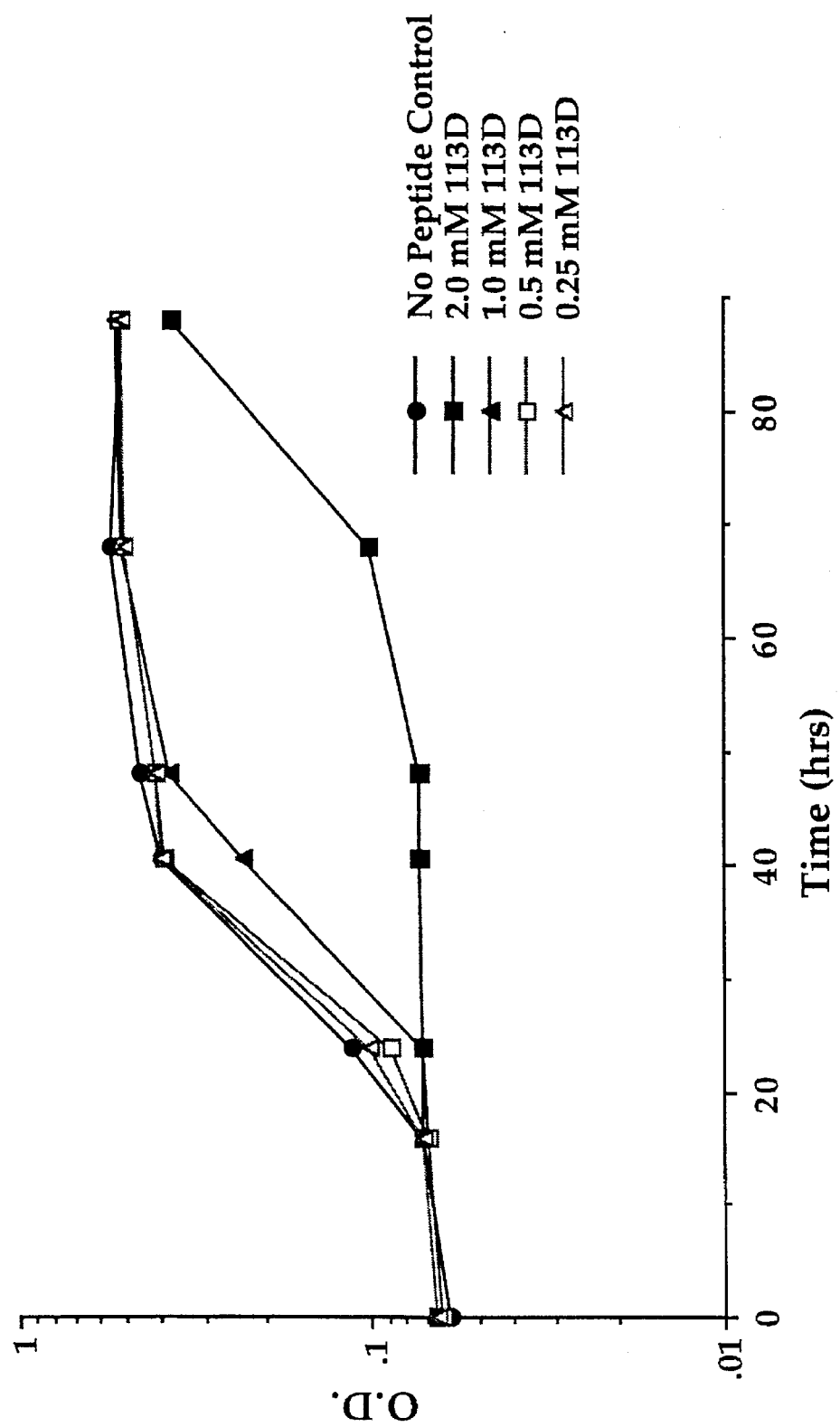
FIG. 5 is a graph that shows the amount of growth inhibition of *P. gingivalis* as a function of time for different concentrations of peptide 113D, as well as when no histatin-based peptide is present.

The peptides described herein were tested in assays designed to measure separately their effectiveness in killing of blastoconidia of *C. albicans*, in inhibiting the growth of *P. gingivalis* and in inhibiting clostripain activity. These assays are indicative of anti-fungal and anti-bacterial activities of the D-amino acid histatin-based peptides of the present invention. When tested in these assays, the D-amino acid histatin-based peptides of this invention were found surprisingly to have superior anti-candidal and anti-bacterial activity in comparison to the natural L-amino form of the histatin-based peptides (see FIG. 4) These anti-fungal and anti-bacterial activities are surprising in view of the size and truncated peptide form of some of these D-amino acid peptides.

The following is a description of the D-amino acid histatin-based peptides, the antifungal activities of the D-amino acid histatin-based peptides as measured in assays for killing of Candida blastoconidia, and the anti-bacterial activities of the histatin-based peptides as measured in assays for inhibition of P. gingivalis growth and inhibition of clostripain enzyme activity.

In the ensuing description, the D-amino acid histatins or histatin-based peptides will be designated by a D following the histatin or histatin-based peptide number, e.g. 113D.

D-Amino Acid Histatin-Based Peptides

The D-version of histatin-based peptide 113 (see FIG. 1A-1C for the amino acid sequence) was prepared using standard solid-phase peptide synthesis techniques (see B. Merrifield, Science 232:241-247 (1986)). In this instance, the carboxyl-terminal amino acid, histidine, which was attached to the solid support, was the L-enantiomer. The D-enantiomer was used for each of the remaining 11 residues, which were sequentially added to the L-histidine on the solid support to form the full length peptide. The resulting peptide was designated as 113D.

Solid supports can be obtained with D-amino acids covalently attached; thus, D-peptides can be prepared such that all residues, including the carboxyl-terminal residue, are the D-enantiomer.

This synthesis technique also allows the artisan to be selective in designating which amino acids are to be the D-enantiomer. In this manner, histatin-based peptides as well as histatins themselves can be synthesized with specific amino acids being of the D-enantiomeric form.

Anti-Fungal Activities of D-Amino Acid Histatin-Based Peptides

C. albicans is a dimorphic yeast. It can exist in a yeast or blastoconidial form, which upon germination develops into the hyphal or germinated form. While the germinated form is considered to be more invasive, most of the C. albicans isolates harvested from the oral cavities of healthy individuals appear to be in the blastoconidial form. (Arendorf, T. M. et al. (1980), Arch. Oral Biol. 25:1-10; Gow, N. A. R. et al. (1987), Criti. Rev. Microbiol. 15:73-78; Odds, F. C. (1988), Candida and Candidosis, 2nd ed., Bailliere Tindall, London, England). Anti-fungal activity of synthetic histatin 5, histatin-based peptide 113, synthetic peptide 113D and histatin-based peptide 129 was measured in assays designed to test the effectiveness of the peptides against the blastoconidia form of Candida. These assays, which measure killing of blastoconidia of C. albicans, are described in Xu et al., which is herein incorporated by reference. (Xu, T. et al. (1991), Infect. Immun. 59(8):2549-2554). Peptide 113D was found to be about equipotent with histatin 5, demonstrating its anti-fungal activity despite its size in comparison with histatin 5. Peptides 113 and 103 demonstrated fungicidal activity comparable to that of histatin 5 and D-amino acid histatin-based peptide 113D. Histatin-based peptide 129 has demonstrable fungicidal activity even though it is smaller than peptide 113. The anti-fungal potency of the histatin-based peptides appear to be a function of both the size and the amino acid sequence of the respective peptide. In particular, the anti-fungal potency of human histatins appears to reside in peptide 113 with selected subpeptides of peptide 113 maintaining at least partial anti-fungal activity. The D-amino acid version of peptide 113 retains the anti-fungal activity of peptide 113.

Therapeutic Applications

The D-amino acid histatins and histatin-based peptides of this invention can be used in compositions and methods of treatment for fungal, and in particular, candidal infection, or for bacterial infection. These methods of treatment for fungal or bacterial infection apply to preventive treatment as well. The compositions may contain combinations of D-amino acid forms and non-D-amino acid forms of histatin-based peptides, in order to obtain maximum activity against all developmental forms of the fungus. The ionic strength, presence of various mono- and divalent ions, and pH of the compositions may be adjusted to obtain maximum anti-fungal or anti-bacterial activity of the histatin-based peptides, as described in Xu et al. (Xu, T. et al. (1991), Infect. Immun. 59(8):2549-54). Carriers appropriate for administration of anti-fungal agents to the vagina, the urethra, the oral cavity, the ophthalmic region and skin are known, and described, for instance, in U.S. Pat. No. 4,725, 576 (Fungicidal Polypeptide Compositions Containing L-His and Methods for Use Therefor by J. J. Pollock and B. J. MacKay, Feb. 16, 1988). Compositions for treatment of systemic infection can be administered by various routes, such as intravenously or subdermally.

The compositions and methods for treatment of fungal or bacterial infections discussed above are not limited to use in humans, but can have veterinary applications as well.

Furthermore, the above-described compositions and methods for treatment of fungal infection can also be used for treatment of bacterial infections (e.g., of S. mutans or P. gingivalis) and viral infections (e.g., of herpex simplex virus or human immunodeficiency virus type 1).

Clostripain Inhibition by D-Amino Acid Histatin-Based Peptides

Figure 6:
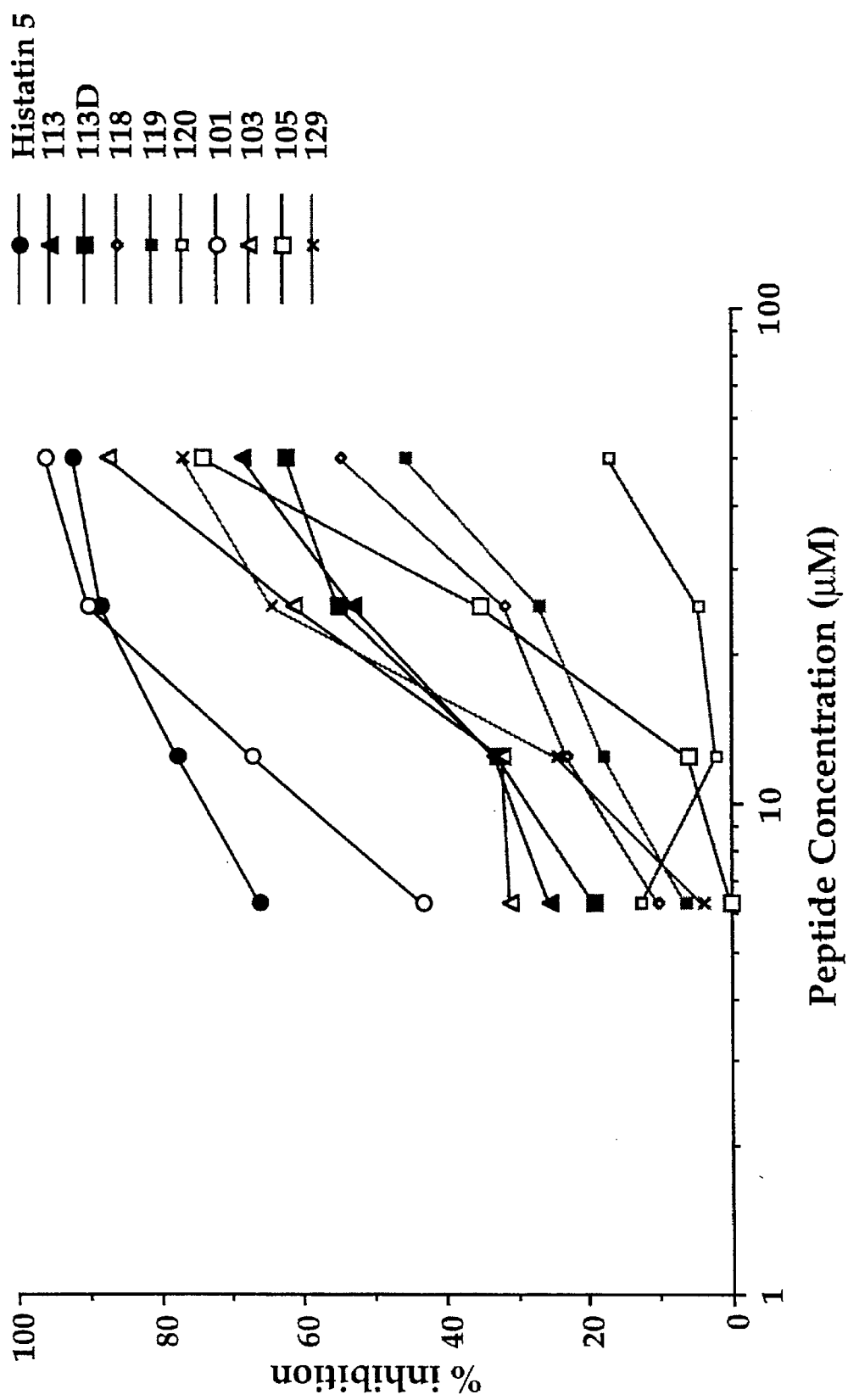
FIG. 6 is a graph that shows the % inhibition of clostripain activity as a function of the concentration of histatin 5, peptide 101, peptide 103, peptide 105, peptide 118, peptide 119, peptide 120, peptide 129, peptide 113 and peptide 113D.

Clostripain is an endopeptidase enzyme synthesized by Clostridium histolyticum. This enzyme, with its protein degradative activity, can be inhibited by histatin 5 and by histatin-based peptides (see FIG. 6). Thus, D-amino acid histatin-based peptides can inhibit bacterial function by inhibiting bacterial enzymes which are essential for the bacterial viability.

EXAMPLE 1

MATERIALS AND METHODS

A. Chemical Synthesis of Histatin-Based Peptides Histatin-based peptides were synthesized by the solid phase method of Merrifield. (Merrifield, B. (1986) Science 232:341-47). Peptides were synthesized by a MilliGen/Bioresearch Sam-Two Peptide Synthesizer using Fmoc L-amino acid kits (Millipore, Bedford, Mass.) and purified on a TSK ODS-i20T $C_{18}$ column (5 μm, 4.6×250 mm) using RP-HPLC (Pharmacia-LKB). The purified peptides were quantified by amino acid analysis on a Beckman System 6300 amino acid analyzer.

B. C. albicans Killing (1) C. albicans Stock

A well-described strain of C. albicans was used in the bioassay. This strain, ATCC 44505, was originally isolated from the human oral cavity. Cultures were stored at 4° C. on Sabouraud dextrose agar plates (Difco Laboratories, Detroit, Mich.) until use. Stationary phase growth cells were obtained following growth at 30° C. for 18 h on Sabouraud dextrose agar plates. Colonies were harvested and suspended in 10 mM potassium phosphate buffer (PPB), pH 7.4.

To initiate log phase growth, an aliquot of stock C. albicans was suspended in Sabouraud dextrose broth (Difco) and incubated at 30° C. in a shaking water bath. The growth phase was determined by taking aliquots of the culture at one hour intervals to monitor the optical density (O.D.) at 560 nm. Early log phase was obtained at 4 to 6 h, indicated by an O.D. of about 0.6. Log phase cells were harvested and utilized in the blastoconidia killing assay in a manner identical to that described for stationary phase cells. A final concentration of $10^5$ cells/ml (either stationary or log phase fungus) was used in all assays.

(2) Suspension Buffers

The standard suspension buffer utilized in the blastospore killing assay was 0.01M PPB, pH 7.4. An alternate suspension buffer, N-2-hydroxyethylpiperazine-N'-2-ethanesulfonic acids (HEPES; Sigma Chemical Co., St. Louis, Mo.), pH 7.4, can also be utilized.

(3) Bioassays

The following assay was used to evaluate the effects of histatins on the killing of blastoconidia of C. albicans.

a. For the killing of blastoconidia assay, 50 μl aliquots of cells ($2 \times 10^5$ cells/ml) diluted in suspension buffer were allowed to attach to a polystyrene 96-well micro-titer plate (COSTAR, Cambridge, Mass.) for 15 min at room temperature, and then incubated with an equal volume of a histatin or histatin peptide in suspension buffer for 1 h at 37° C. Controls were carried out in the absence of the histatin or histatin peptide. After incubation, wells were washed three times by centrifugation at 1.000×g for 5 min and covered with aliquots of molten Sabouraud dextrose broth (Difco) containing 2% agarose (Sigma) at 45° C. The plate was then incubated at 30° C. for 8 h. Under such conditions, live cells will divide and begin to form colonies, while dead cells will remain as single cells. To determine the percentage of blastoconidia killed, a total of 100 single cells and/or colonies were counted under a Nikon inverted microscope at 400×magnification and the extent of killing was calculated using the formula: [1−(number of colonies in treated sample)/(number of colonies in control)]×100%.

(4) Statistical Analysis

Data were obtained by calculating the mean and standard deviation from triplicate assays. From the dose response relationship, doses effecting a 50% killing ($LD_{50}$).

C. BACTERIAL GROWTH INHIBITION ASSAY (1) Bacterial Strains and Culture Conditions The bacteria used in this investigation, *Porphyromonas gingivalis* strain A7A1-28, is a typical key pathogenic organism associated with destructive periodontal diseases. The bacteria were multiply subcultured in Enriched Todd Hewitt broth (ETHB, Difco Lab., Detroit, Mich.). Microorganisms were stored in the same broths containing 20% and 50% glycerol, at −20° C. and −70° C., respectively. These served as stock cultures from which all preparations originated.

Working stock cultures were maintained by weekly transfer to Brain Heart Infusion Anaerobic Sheep Blood Agar plates (BHIA, Becton Dickinson and Co., Cockeysville, Md.), and Trypticase Soy Anaerobic Sheep Blood Agar plates (TSA, Becton Dickinson and Co., Cockeysville, Md.). Plates were incubated for 3 to 4 days under strictly anaerobic conditions. For the bacteriostatic assay, bacteria were collected from plates, inoculated into the aforementioned broth and grown at 37° C., under strictly anaerobic conditions for 24 to 48 hours.

(2) Microdilution Bacteriostatic Assay

A modification of the typical microdilution assay (Rotilie et al., 1975) for the determination of minimal inhibitory concentration (MIC) of antimicrobial agents was utilized to investigate the bacteriostatic activity of the peptides. A standardized bacterial inoculum was exposed to serially diluted antimicrobial peptides in an enriched broth medium that was suitable for the growth of anaerobic bacteria. The test was adapted for use in the 96-well microtiter plates. Results with the microdilution method have been shown to be comparable to the other known techniques for antimicrobial susceptibility such as the dilution method, the agar dilution method, and the broth-disk elution method (Rosenblatt et al., 1979). In the typical assay, the microtiter plate was observed at multiple time points after incubation for visible growth. The modification introduced here was based on the spectrophotometric reading of the microtiter plate after incubation.

Microorganisms from cultures maintained in the aforementioned plates were inoculated into 5 ml of the above-mentioned broths and cultured overnight at 37° C. under strictly anaerobic conditions with continuous agitation on a minishaker (IKA-Labortechnik, Staufen i. Br., Germany). The bacteria were grown until reaching the late log phase and were then suspended in the same broths to an optical density (O.D.) of 0.1 at 560 nm. The peptides were diluted in 0.01M phosphate buffered saline (PBS), pH 7. Forty μl aliquots of peptide dilutions were added in each well of a U-bottom microtiter plate (Costar, Cambridge, Mass.) to give final concentrations of 2000, 1000, 500 and 250 μM. Twenty μl of bacterial inoculum was added to all the wells. Finally, 100 μl of the suitable broth were added to each well. The optical density of the wells of the microtiter plate was determined using a microplate reader set at 550 nm and the plate was then incubated under strictly anaerobic conditions for 24 hours. Controls were made by replacing the peptide dilutions with PBS alone. After the incubation, the mixtures in each well were mixed manually to resuspend sedimented bacteria and the plate was read again. The experiments were conducted twice every time. The biologic activity was calculated according to the formula:

$$100-[[(\text{Fin ODexp-In ODexp})/(\text{Fin ODctr-In ODctr})] \times 100]$$

where:

Fin ODexp is the OD of the final experimental group;

In ODexp is the OD of the initial experimental group;

Fin ODctr is the OD of the final control group; and

In ODctr is the OD of the initial control group.

In addition, the % increase in time to reach mid-log phase growth was calculated.

The data presentation represent the means (±SEM) of at least 2 separate experiments.

D. CLOSTRIPAIN ASSAYS

Clostripain from *Clostridium histolyticum* (Sigma Chemical Corp., St. Louis, Mo.) was dissolved in deionized water to a concentration of 1 mg/mL (300 units/mg) and activated with the addition of 10 mmol/L DTT. To measure its hydrolytic activity, clostripain (6 units) was added to 50 nmol/L Hepes buffer, pH 7.5, containing 80 μmol/L BAPNA (benzoyl-arginine-p-nitroanilide), together with 5.6 μmol/L of histatin peptide inhibitor. As controls, assays were performed in the absence of any histatin peptide inhibitor. The activity was monitored continuously at 405 nm using a Molecular Devices $V_{Max}$ microtitre plate reader. The activities were determined from the maximum rates of substrate hydrolysis. Assays were done in duplicate, and the means normalized to the controls.

EXAMPLE 2

EFFECTS OF HISTATIN PEPTIDES, INCLUDING D-AMINO ACID HISTATIN-BASED PEPTIDES, ON FUNGAL OR BACTERIAL VIABILITY

FIGS. 2–6 summarize the results of the fungal killing, bacterial growth inhibition and bacterial enzyme (clostripain) inhibition effects of D-amino acid histatin-based peptide 113D and several tested histatin peptides. For comparison purposes, the anti-fungal and anti-bacterial effects of peptide 113D and the non-D-amino acid histatin-based peptides were assessed with synthesized histatin 5 as a standard. Peptide 113D and histatin-based peptides 113, 118, 119, 120 and 129 have *C. albicans* blastoconidia killing, *P. gingivalis* growth inhibition and clostripain inhibition effects. These antimicrobial effects are similar to those observed for histatin 5 and for histatin-based peptides 101–105. Although expected variations exist in anti-fungal and anti-bacterial effects between the tested peptides, the antimicrobial effects of the D-amino acid histatin-based peptides are comparable to those of histatin 5. These results demonstrate that D-amino acid histatin-based peptides are efficacious as anti-fungal or anti-bacterial agents. In particular, it should be noted that peptide 113D is efficacious for a longer period of time than its L-enantiomer congener (see FIG. 4). Thus, it is anticipated that the D-amino acid histatin-based peptides will have advantageous uses in comparison to L-enantiomeric histatin-based peptides. One of the reasons for this efficacy is that the D-amino acid form is less susceptible to biological degradation.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition for treating a fungal or bacterial infection comprising a histatin-based peptide having an amino acid sequence of at least eight amino acids and comprising one or more D-amino acids wherein,
a) the amino acid sequence of histatin 9 as set forth in SEQ ID NO: 9;
b) the amino acid sequence of peptide 101 as set forth in SEQ ID NO: 13;
c) the amino acid sequence of peptide 102 as set forth in SEQ ID NO: 14;
d) the amino acid sequence of peptide 103 as set forth in SEQ ID NO: 15;
e) the amino acid sequence of peptide 104 as set forth in SEQ ID NO: 16;
f) the amino acid sequence of peptide 105 as set forth in SEQ ID NO: 17;
g) the amino acid sequence of peptide 113 as set forth in SEQ ID NO: 18;
h) the amino acid sequence of histatin 11 as set forth in SEQ ID NO: 11;
i) the amino acid sequence of peptide 129 as set forth in SEQ ID NO: 23;
j) the amino acid sequence of peptide 117 as set forth in SEQ ID NO: 19;
k) the amino acid sequence of peptide 118 as set forth in SEQ ID NO: 20;
l) the amino acid sequence of peptide 119 as set forth in SEQ ID NO: 21;
m) the amino acid sequence of peptide 120 as set forth in SEQ ID NO: 22; and
n) combinations of two or more of the above.

2. A histatin-based peptide having an amino acid sequence of at least eight amino acids and comprising one or more D-amino acids wherein,
a) the amino acid sequence of histatin 9 as set forth in SEQ ID NO: 9;
e) the amino acid sequence of peptide 101 as set forth in SEQ ID NO: 13;
c) the amino acid sequence of peptide 102 as set forth in SEQ ID NO: 14;
d) the amino acid sequence of peptide 103 as set forth in SEQ ID NO: 15;
e) the amino acid sequence of peptide 104 as set forth in SEQ ID NO: 16;
f) the amino acid sequence of peptide 105 as set forth in SEQ ID NO: 17;
g) the amino acid sequence of peptide 113 as set forth in SEQ ID NO: 18;
h) the amino acid sequence of histatin 11 as set forth in SEQ ID NO: 11;
i) the amino acid sequence of peptide 129 as set forth in SEQ ID NO: 23;
j) the amino acid sequence of peptide 117 as set forth in SEQ ID NO: 19;
k) the amino acid sequence of peptide 118 as set forth in SEQ ID NO: 20;
l) the amino acid sequence of peptide 119 as set forth in SEQ ID NO: 21;
m) the amino acid sequence of peptide 120 as set forth in SEQ ID NO: 22; and
n) combinations of two or more of the above.

3. A method for treating a fungal or bacterial infection in an individual comprising administering to said individual a therapeutically effective amount of at least one histatin based peptide having an amino acid sequence of at least eight amino acids and comprising one or more D-amino acids wherein said peptide,
a) the amino acid sequence of histatin 9 as set forth in SEQ ID NO: 9;
b) the amino acid sequence of peptide 101 as set forth in SEQ ID NO: 13;
c) the amino acid sequence of peptide 102 as set forth in SEQ ID NO: 14;
d) the amino acid sequence of peptide 103 as set forth in SEQ ID NO: 15;
e) the amino acid sequence of peptide 104 as set forth in SEQ ID NO: 16;
f) the amino acid sequence of peptide 105 as set forth in SEQ ID NO: 17;
g) the amino acid sequence of peptide 113 as set forth in SEQ ID NO: 18;
h) the amino acid sequence of histatin 11 as set forth in SEQ ID NO: 11;
i) the amino acid sequence of peptide 129 as set forth in SEQ ID NO: 23;
j) the amino acid sequence of peptide 117 as set forth in SEQ ID NO: 19;
k) the amino acid sequence of peptide 118 as set forth in SEQ ID NO: 20;
l) the amino acid sequence of peptide 119 as set forth in SEQ ID NO: 21; and
m) the amino acid sequence of peptide 120 as set forth in SEQ ID NO: 22.

4. A method for treating a fungal or bacterial infection of claim 3 wherein said fungal or bacterial infection is selected from the group consisting of:
a) an infection of the oral cavity;
b) an infection of the vagina;
c) an infection of the urethra;
d) an infection of the skin;
e) an ophthalmic infection; and
f) a systemic infection.

5. A method for treating a fungal or bacterial infection of claim 4 wherein the fungus or bacterium is selected from the group consisting of:
a) *Candida albicans;*
b) *Actinomyces actinomycetemcomitans;*
c) *Actinomyces viscosus;*
d) *Bacteroides forsythus;*
e) *Bacteriodes fragilis;*
f) *Bacteriodes gracilis;*
g) *Bacteriodes ureolyticus;*
h) *Campylobacter concisus;*
i) *Campylobacter rectus;*
j) *Campylobacter showae;*
k) *Campylobacter sputorum;*
l) *Capnocytophaga gingivalis;*
m) *Capnocytophaga ochracea;*
n) *Capnocytophaga sputigena;*
o) *Clostridium histolyticum;*
p) *Eikenella corrodens;*
q) *Eubacterium nodatum;*
r) *Fusobacterium nucleatum;*
s) *Fusobacterium periodonticum;*
t) *Peptostreptococcus micros;*
u) *Porphyromonas endodontalis;*
v) *Porphyromonas gingivalis;*
w) *Prevotella intermedia;*
x) *Prevotella nigrescens;*
y) *Propionibacterium aches;*
z) *Pseudomonas aeruginosa;*
aa) *Selenomonas noxia;*
bb) *Staphylococcus aureus;*
cc) *Streptococcus constellatus;* dd) *Streptococcus gordonii;*
ee) *Streptococcus intermedius;*
ff) *Streptococcus mutans;*
gg) *Streptococcus oralis;*
hh) *Streptococcus pneumonia;*
ii) *Streptococcus sanguis;*
kk) *Treponema denticola;* ll) *Treponema pectinovorum;*
mm) *Treponema socranskii;*
nn) *Veillonella parvula;* and
oo) *Wolinella succinogenes.*

* * * * *

UNITED STATES PATENT AND TRADEMARK OFFICE
CERTIFICATE OF CORRECTION

PATENT NO. : 5,646,119
DATED : July 8, 1997
INVENTOR(S) : Frank G. Oppenheim, Tao Xu and Peter Spacciopoli It is certified that error appears in the above-identified patent and that said Letters Patent is hereby corrected as shown below:

| | |
|---|---|
| In Column 23, line 5: | After the word "wherein", delete the comma and insert the words --said peptide is selected from the group consisting of:--; |
| In Column 23, line 34: | After the word "wherein", delete the comma and insert the words --said peptide is selected from the group consisting of:--; |
| In Column 23, line 67: | After the word "peptide", delete the comma and insert the words --is selected from the group consisting of:--; and |
| In Column 24, line 63: | After the word "*Propianibacterium*", delete the word "*aches*" and insert the word --*acnes*-- therefor. |

Signed and Sealed this

Seventh Day of October, 1997

*Attest:*

BRUCE LEHMAN

*Attesting Officer*   *Commissioner of Patents and Trademarks*